United States Patent [19]

Ohachi

[11] Patent Number: 4,740,545
[45] Date of Patent: Apr. 26, 1988

[54] POLYVINYL CHLORIDE RESIN COMPOSITION FOR MEDICAL INSTRUMENTS

[75] Inventor: Yoshinori Ohachi, Fujinomiya, Japan

[73] Assignee: Terumo Kabushiki Kaisha, Tokyo, Japan

[21] Appl. No.: 930,276

[22] Filed: Nov. 12, 1986

Related U.S. Application Data

[62] Division of Ser. No. 743,510, Jun. 11, 1985.

[30] Foreign Application Priority Data

Jun. 18, 1984 [JP] Japan ................................ 59-123669
Jun. 18, 1984 [JP] Japan ................................ 59-123670

[51] Int. Cl.$^4$ .............................................. C08K 5/11
[52] U.S. Cl. ..................................................... 524/314
[58] Field of Search ........................................ 524/314

[56] References Cited

U.S. PATENT DOCUMENTS

| | | | |
|---|---|---|---|
| 3,219,729 | 11/1965 | Meyers et al. | 525/207 |
| 3,901,839 | 8/1975 | Lovering | 525/83 |
| 4,077,935 | 3/1978 | Wszolek | 524/290 |
| 4,111,889 | 9/1978 | Kaneko et al. | 524/314 |
| 4,143,011 | 3/1979 | Hisazumi et al. | 524/314 |
| 4,184,993 | 1/1980 | Singh et al. | 524/314 |
| 4,301,800 | 11/1981 | Collins | 128/DIG. 24 |
| 4,401,720 | 8/1983 | Davis et al. | 523/523 |
| 4,421,885 | 12/1983 | Tsuda et al. | 524/111 |

FOREIGN PATENT DOCUMENTS

| | | | |
|---|---|---|---|
| 591692 | 2/1960 | Canada | 524/314 |
| 897857 | 4/1972 | Canada | 524/314 |
| 1058670 | 6/1959 | Fed. Rep. of Germany | 524/314 |
| 1012226 | 7/1952 | France . | |
| 49-130444 | 12/1974 | Japan | 524/314 |
| 1148357 | 4/1969 | United Kingdom . | |

OTHER PUBLICATIONS

H. Kopsch "Der Einflub der Weichmacher-Struktur auf die thermische Stabilitat vonWeich-PVC-Mischungen", Kunststoffe 67 (1977)3, pp. 141-145.

Primary Examiner—Joseph L. Schofer
Assistant Examiner—N. Sarofim
Attorney, Agent, or Firm—Frishauf, Holtz, Goodman & Woodward

[57] ABSTRACT

A polyvinyl chloride composition comprising component (1) 100 parts by weight of polyvinyl chloride, component (2) 0.1 to 50 parts by weight of an unsaturated aliphatic dicarboxylic dialkyl ester represented by the general formula I: $R_1OCOCR_3=CR_4COOR_2$ wherein $R_1$ and $R_2$ independently denote an alkyl group having 1 to 15 carbon atoms and $R_3$ and $R_4$ independently denote a group represented by the general formula II: $-C_nH_{2n+1}$ wherein n denotes an integer of the value of 0 to 6, and component (3) 0 to 200 parts by weight of a plasticizer which is not said component (2).

19 Claims, No Drawings

POLYVINYL CHLORIDE RESIN COMPOSITION FOR MEDICAL INSTRUMENTS

This is a division of application Ser. No. 743,510 filed June 11, 1985.

BACKGROUND OF THE INVENTION

1. Field of the Invention

This invention relates to a vinyl chloride resin composition and a medical instrument made of the resin composition. More particularly, this invention relates to a vinyl chloride resin composition which enjoys high safety and exhibits high stability to withstand heat, light, and radiation and to a medical instrument made of the resin composition and enabled to be sterilized safely with radioactive ray.

2. Description of the Prior Art

Generally, vinyl chloride resin excels in workability, physiological safety, and transparency and features low price and, therefore, finds widespread utility as a resin for the production of various medical instruments such as bags for blood, bags for transfusion fluids, and conduits for blood transfer.

The vinyl chloride resin, however, suffers from the serious drawback of succumbing to thermal decomposition. By the action of heat, the vinyl chloride resin is caused to undergo decomposition due to removal of hydrochloric acid by some mechanism yet to be elucidated. In the air, it is oxidized and caused to undergo molecular cleavage and cross-linking bonding at a sacrifice of physical properties including freedom from brittleness.

The tendancy of the vinyl chloride resin for degradation by heat naturally entails various problems.

When a vinyl chloride resin piece is fabricated in a given shape, especially when the vinyl chloride resin is of rigid grade or of high polymerization degree, since it has high melt viscosity and generates heat of friction heavily, the resin temperature rises sharply and, consequently, undergoes accelerated thermal decomposition and, during the course of fabrication, suffers from thermal deterioration within the molding machine. When the resin happens to undergo lengthy residence within the molding machine, such resin manifests itself as a black extraneous portion in the shaped article obtained by the fabrication. When the vinyl chloride resin is exposed to high shearing strength during the course of fabrication as in injection molding, the resin under treatment is tarnished in part to impair the outward appearance of the shaped article resulting from the fabrication. Thus, the shaped article is rejectable as an item of commerce. Moreover, there is the possibility that the interior of the molding machine must be cleaned frequently for removal of the stagnant resin.

Further, the vinyl chloride resin possesses the serious drawback of being degraded by light and radiation. To be more specific, by the action of heat or radiation of wavelength of not more than 3,000 A, it undergoes decomposition due to removal of hydrochloric acid by some mechanism yet to be elucidated. As the decomposition starts, it accelerates removal of hydrochloric acid in the manner of chain reaction and brings about sequential formation of a conjugate double bond otherwise called a polyene structure (zipper reaction). It is generally held that when 8 or more double bonds form a chain within the conjugate polyene, they form a chromophore within the visible zone [Hirayama: Journal of Japan Chemical Society, 75, 27, 667 (1954)] and cause coloration of the resin. As this reaction proceeds, the resin grows black and entails molecular cleavage and cross-linking bonding and can no longer withstand impacts inflicted during daily use.

This tendancy of the vinyl chloride resin toward degradation by the action of heat, light, and radiation naturally entails various problems detrimental to the use of this resin in apparatus for medical treatment.

For example, as a flexible vinyl chloride resin composition for use in a medical instrument, the vinyl chloride composition which comprises 100 parts by weight of polyvinyl chloride, 30 to 80 parts by weight of di-2-ethylhexyl phthalate, 0.01 to 5 parts by weight of a calcium-zinc type stabilizer, 0 to about 10 parts by weight of epoxidized soybean oil as a stabilizing aid, and optionally 0 to about 5 parts by weight of lubricant, etc, has been provided to date.

When any of these medical instrument is sterilized by means of radiation, the vinyl chloride resin is deteriorated by exposure to radiation and, consequently, is discolored with passage of time to the point of becoming unsuitable for use as a medical instrument.

Unlike the method of thermal sterilization which requires the apparatus to possess high resistance to heat and yield minimally to heat distortion or unlike the method of sterilization by the use of a bactericide such as ethylene oxide gas which requires the treated apparatus to be left standing long before it becomes fit for safe handling, the method of sterilization by radiation is excellent in the sense that the sterilization can be carried out easily at low temperature. Despite the characteristic feature, this method is not safely applicable to the vinyl chloride resin.

Numerous studies have been made to date for improving to a sufficient extent the stability of the vinyl chloride resin to withstand heat, light, and radiation. One such study has led to acquisition of the knowledge that an organic compound of such heavy metal as lead or cadmium is highly effective in stabilizing the vinyl chloride resin. Since the organic compound of such a heavy metal as described above is highly toxic and, therefore, harmful to man, it cannot be incorporated in the material for apparatus for medical treatment. The vinyl chloride resin composition which is now accepted generally for use in medical instrument incorporates a metallic soap tye stabilizer of calcium or zinc which is held not to be toxic. The stability improved by the use of such a stabilizer as described above is not sufficient.

As an organic stabilizer there is a report [W. Szymanski, G. Smietanska, journal of Applied Polymer Science, 19, 1955 (1975)] that a $\beta$-aminocrotonic ester is effective in improving the stability of the reisn to withstand radiation and in repressing the removal of hydrochloric acid. The medical instrument made of vinyl chloride resin incorporating the $\beta$-aminocrotonic ester as a stabilizer, on being sterilized with radiation, is discolored to a greater extent than the apparatus not containing this organic stabilizer in the resin. Thus, this aparatus fails to satisfy the standard of safety and does not fit medical use. In the case of a medical instrument made of vinyl chloride resin incorporating $\beta$-diketone (product of Rhone Poulenc marketed under trademark designation of Carrens DK-1), a substance claimed to be a highly effective color inhibitor, when this apparatus is sterilized by radiation, it is discolored to the same extent as or to a greater extent than the apparatus made of vinyl chloride resin not incorporating this color inhibitor. Thus, this apparatus also does not fit applications requiring sterilization by radiation.

An object of this invention, therefore, is to provide an improved vinyl chloride resin composition and a medical instrument which is made of the vinyl chloride resin composition.

Another object of this invention is to provide a vinyl chloride resin composition enjoying high safety and exhibiting high stability to withstand heat, light, and radiation and a medical instrument which is made of the resin composition.

Yet another object of this invention is to provide a vinyl chloride resin composition which exhibits improved dynamic thermal stability during the course of fabrication.

A further object of this invention is to provide a medical instrument which can be safely and effectively sterilized by radiation.

SUMMARY OF THE INVENTION

The various objects of this invention described above are accomplished by a vinyl chloride resin composition, which comprises 100 parts by weight of vinyl chloride resin, 0.1 to 50 parts by weight of an unsaturated aliphatic dicarboxylic dialkyl ester represented by the general formula I:

wherein $R_1$ and $R_2$ independently denote an alkyl group having 1 to 15 carbon atoms and $R_3$ and $R_4$ independently denote a group represented by the general formula II: $-C_nH_{2n+1}$ where n denotes an integer of the value of 0 to 6, and 0 to 200 parts by weigh of other plasticizer.

The various objects described above are also accomplished by a medical instrument, which is made of a vinyl chloride resin composition comprising 100 parts by weight of vinyl chloride resin, 0.1 to 50 parts by weight of an unsaturated aliphatic dicarboxylic dialkyl ester represented by the general formula I:

wherein $R_1$ and $R_2$ independently denote an alkyl group having 1 to 15 carbon atoms and $R_3$ and $R_4$ independently denote a group represented by the general formula II: $-C_nH_{2n+1}$ where n denotes an ingeger of the value of 0 to 6, and 0 to 200 parts by weight of another plasticizer and which can be safely sterilized with radiation emitted by a radioactive material.

In one aspect, this invention relates to a vinyl chloride resin composition and a medical instrument which both satisfy the general formula II on condition that the symbol n in the formula is 1 or 0. In another aspect, this invention relates to a vinyl chloride resin composition and a medical instrument which both satisfy the general formula I on condition that the symbols $R_3$ and $R_4$ each denote hydrogen atom. In yet another aspect, this invention relates to a vinyl chloride resin composition and a medical instrument which both satisfy the general formula I on condition that either of the symbols $R_3$ and $R_4$ denotes a methyl group and the other symbol denotes hydrogen atom. In a further aspect, this invention relates to a vinyl chloride resin composition and a medical instrument which both satisfy the general formula I on condition that the alkyl goups in the substituents $R_1$ and $R_2$ each has 3 to 15 carbon atoms. In another aspect, this invention relates to a vinyl chloride resin composi- tion and a medical instrument which both have a maleic dialkyl ester or a fumaric dialkyl ester as the unsaturated dicarboxylic dialkyl ester. In yet another aspect, this invention relates to a vinyl chloride resin composition and a medical instrument which both incorporate the maleic dialkyl ester or fumaric dialkyl ester in a proportion of 0.5 to 40 parts by weight. In still another aspect, this invention relates to a vinyl chloride resin composition and a medical instrument which both have dioctyl maleate, dibutyl maleate, dioctyl fumarate, or dibutyl fumarate as the unsaturated aliphatic dicarboxylic dialkyl ester.

Further in one aspect, this invention relates to a vinyl chloride resin composition and a medical instrument which both incorporate dioctyl maleate or dioctyl fumarate in a proportion of 2 to 40 parts by weight. In another aspect, this invention relates to a vinyl chloride resin composition and a medical instrument which both incorporate dibutyl maleate or dibutyl fumarate in a proportion of 0.5 to 20 parts by weight. In a further aspect, this invention relates to a vinyl chloride resin composition and a medical instrument which both have a phthalic dialkyl ester (each of the alkyl groups of which has 6 to 13 carbon atoms) as the plasticizer. In a yet further aspect, this invention relates to a vinyl chloride resin composition and a medical instrument which both an epoxy-hexahydrophthalic dialkyl ester as the plasticizer.

DESCRIPTION OF THE PREFERRED EMBODIMENT

The vinyl chloride resin composition according to the present invention is used advantageously in sheets, pipes, containers, and various medical instrument, especially in medical instrument.

Typical examples of the medical instrument contemplated by the present invention include containers for holding body fluids, medical apparatus such as catheters, blood transfusion sets, fluid transfusion sets, and conduits for blood transfer, containers for packing medical instrument, and containers for wrapping tablets.

Examples of the vinyl chloride resin to be used in the vinyl chloride resin composition according to the present invention include homopolymer of vinyl chloride, polyvinylidene chloride, and copolymer of at least 40% by weight, more desirably at least 65% by weight, and most desirably at least 75% by weight, of vinyl chloride and another copolymerizable monomer. The average polymerization degree of the vinyl chloride resin is in the range of 400 to 3,000, more desirably 600 to 2,700, and most desirably 800 to 1,700. Examples of the comonomer which forms the copolymer with vinyl chloride include vinylidene chloride, ethylene, propylene, vinyl acetate, vinyl bromide, vinyl fluoride, styrene, vinyl toluene, vinyl pyridine, acrylic acid, alkyl acrylates (such as methyl acrylate, ethyl acrylate, isopropyl acrylate, n-butyl acrylate, and 2-ethylhexyl acrylate), methacrylic acid, alkyl methacrylates (such as methyl methacrylate, ethyl methacrylate, and 2-ethylhexyl methacrylate), acrylonitrile, and methacrylonitrile. Optionally, the vinyl chloride resin may incorporate therein styrene-acrylonitrile copolymer or styrene-methacrylonitrile copolymer.

The salient characteristic of the present invention resides in the fact that the vinyl chloride resin incorporates therein an unsaturated aliphatic dicarboxylic dialkyl ester represented by the general formula I.

$$R_1OCOCR_3=CR_4COOR_2 \tag{I}$$

It is surprising to note that when the unsaturated dicarboxylic dialkyl ester is added to the vinyl chloride resin, the tendency of the vinyl chloride resin toward deterioration caused by the action of heat, light, and radiation is notably changed and the stability of the vinyl chloride resin to resist deterioration by exposure to radiation is conspicuously improved. Although the mechanism underlying the enhanced stability remains yet to be elucidated, it is inferred that the following reaction has something to do with the improvement attained in the stability. As already described, by the action of heat, light, or radiation, the vinyl chloride resin is deteriorated to give rise to (1) a conjugate polyene structure. This decomposition occurs in the form of chain reaction. As the removal of hydrochloric acid proceeds and the double bonds of the conjugate polyene structure increase, the resin undergoes coloration. As the reaction further proceeds, the resin grows brown and eventually turns black. When, in this case, the unsaturated aliphatic dicarboxylic dialkyl ester of the general formula I is present in the vinyl chloride resin, this unsaturated aliphatic dicarboxylic dialkyl ester causes a molecular reaction upon the carbon atoms at the n and n+3 positions in (2) the conjugate polyene and effects addition of the unsaturated aliphatic dicarboxylic dialkyl ester to (3) the n and n+3 positions and, consequently, gives rise to a six-member ring.

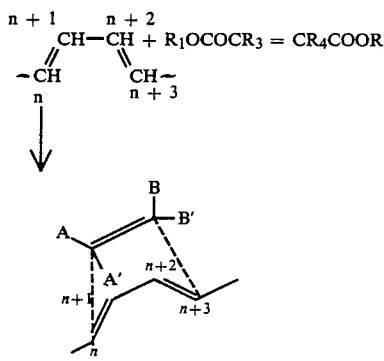

In the formula given above, A and A' independently denote —$R_3$ or —$COOR_1$ and B and B' independently denote —$R_4$ or —$COOR_2$.

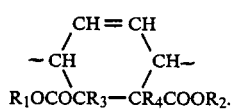

As shown above, the Diels-Alder reaction of a sort occurs between the conjugate polyene in the vinyl chloride resin and the unsaturated aliphatic dicarboxylic dialkyl ester. This reaction is believed to sever the conjugate polyene structure and bring the deterioration to a stop. Typical examples of the unsaturated aliphatic dialkyl ester represented by the general formula I are maleic dialkyl esters, fumaric dialkyl esters, citraconic dialkyl esters, mesaconic dialkyl esters, dimethylmaleic dialkyl esters, and dimethyl-fumaric dialkyl esters. The alkyl group of the unsaturated aliphatic dicarboxylic dialkyl ester has 1 to 15 carbon atoms. When at least either of the two moieties of the unsaturated aliphatic dicarboxylic dialkyl ester is an acid, there is the possibility of the ester constituting a toxic substance. When the number of carbon atoms of the alkyl group exceeds 15, the ability of the ester to enhance the stability of the resin is degraded and the miscibility of the ester with the resin is also impaired. The alkyl groups of $R_1$ and $R_2$ in the general formula I are not reuqired to be identical with each other. They may be alcohol mixture esters of different chain lengths.

In the unsaturated aliphatic dicarboxylic dialkyl ester represented by the general formula I, $R_3$ and $R_4$ independently denote an alkyl group represented by the general formula II:

$$-C_nH_{2n+1} \tag{II}$$

or a hydrogen atom. The length of this alkyl group is not more than 6 carbon atoms ($n \leq 6$). If the number of carbon atoms of the alkyl group is 7 or more, the miscibility of the ester with the vinyl chloride resin is impaired. The alkyl groups of $R_3$ and $R_4$ are not required to be identical with each other.

In the unsaturated aliphatic dicarboxylic dialkyl ester of the foregoing description, the alkyl groups of $R_1$ and $R_2$ in the general formula I each have 1 to 15 carbon atoms, more desirably 3 to 13 carbon atoms, and most desirably 4 to 10 carbon atoms. These alkyl groups may be in a branched form or a straight form. Preferably, they are in a straight form.

Among other unsaturated aliphatic dicarboxylic dialkyl esters, maleic dialkyl esters and fumaric dialkyl esters prove most effective in various respects including economy. Particularly dibutyl maleate, dibutyl fumarate, dioctyl maleate, and dioctyl fumarate are the best selections.

When a medical instrument is made of vinyl chloride resin incorporating either an unsaturated aliphatic dicarboxylic dialkyl ester represented by the general formula III:

$$R_5OCOC(=CH_2)CH_2COOR_6 \tag{III}$$

wherein the hydrogen atom may be substituted with an alkyl group or an unsaturated aliphatic monocarboxylic alkyl ester represented by the general formula IV:

$$CH_2=CHCOOR_7 \tag{IV}$$

wherein the hydrogen atom may be substituted with an alkyl group, thus possessed of a structure similar to the general formula I and, therefore, suspected to be effective similarly to the ester of the present invention, this instrument is heavily colored after exposure to radiation similarly to a medical instrument which omits incorporation of such unsaturated aliphatic carboxylic ester. This fact clearly evinces the essentiality of the unsaturated aliphatic carboxylic ester, as one component for the vinyl chloride resin composition contemplated by the present invention, possessing the structure represented by the general formula I.

The unsaturated aliphatic dicarboxylic dialkyl ester is incorporated in the vinyl chloride resin composition in an amount of 0.1 to 50 parts by weight, preferably 0.5 to 40 parts by weight, based on 100 parts by weight of the vinyl chloride resin.

Particularly dioctyl maleate or dioctyl fumarate incorporated in an amount of 2 to 40 parts by weight or dibutyl maleate or dibutyl fumarate incorporated in an amount of 0.5 to 20 parts by weight proves particularly effective. The unsaturated aliphatic dicarboxylic dialkyl ester so added to the vinyl chloride resin composition serves to confer upon the vinyl chloride resin the stability required to resist heat, light, or radiation and, at the same time, impart thereto the plasticity proportionately to the amount of the ester to be added.

For further improvement of the plasticizing effect, another plasticizer is desired to be added. Any of the plasticizers generally adopted for use with the vinyl chloride resin can be used. Examples of the othere plasticizer used for this purpose include phthalic esters such a dibutyl phthalate (DBP), dihexyl phthalate (DHP), di-2-ethylhexyl phthalate (DOP), di-n-octyl phthalate (DnOP), diisooctyl phthalate (DIOP), diheptyl phthalate, didecyl phthalate (DDP), diisodecyl phthalate (DIDP), didecyl phthalate (DDP), diisodecyl phthalate (DIDP), octyl decyl phthalate, and butyl benzyl phthalate (BBP), trimellitic esters such as tributyl trimetillate and trioctyl trimetillate, aliphatic polybasic acid esters such as dioctyl adipate (DOA), dioctyl azelate (DOZ) and dioctyl sebacate (DOS), phosphoric esters such as tricresyl phosphate (TCP), tirxylenyl phosphate (TXP), monooctyldiphenyl phosphate (Santicizer 141), monobutyl dixylenyl phosphate (B-2-X), and trioctyl phosphate (TOF), citric esters such as tributyl acetyl citrate, trioctyl acetyl citrate, and tributyl citrate, and butyl phthalyl butyl glycolate (BPBG). Among other plasticizers, phthalic dialkyl esters (whose alkyl groups have 6 to 13 carbon atoms) prove particularly desirable. If the number of carbon atoms of the alkyl group in the compound is less than 6, the compound has the possibility of constituting a toxic substance. If this number exceeds 13, the miscibility of the compound with the vinyl chloride resin is inferior. The alkyl group is desired to be of a linear form from the standpoint of safety. The plurality of alkyl groups are not required to be identical with one another. They may be alchol mixture esters of different chain lengths.

Further, any of the epoxy hexahydrophthalic dialkyl esters possessing similar alkyl groups may be advantageously used as a plasticizer.

The plasticizer of the foregoing description is incorporated in an amount of 0 to 200 parts by weight, more desirably 5 to 150 parts by weight, and most desirably 10 to 80 parts by weight, based on 100 parts by weight of the vinyl chloride resin.

Optionally, the vinyl chloride resin composition can incorporate therein a metallic soap of potassium or zinc with stearic acid, lauric acid, ricinolic acid, or naphthenic acid, an epoxidized vegetable oil such as epoxidized soybean oil or epoxidized linseed oil, lubricant, or other antioxidant. As the aforementioned plasticizer, the plasticizer formed of the conventionally known high polymer such as, for example polychloroprene resin or thermoplastic polyurethane resin can be used by the technique of polymer blend.

The radiation which can be used for the sterilization of the medical instrument according with the present invention is an electromagnetic radiation such as gamma ray or electron ray. The gamma ray is more desirable than the electron ray. The intensity of exposure is 1 to 5 Mrads, preferably 1.5 to 3 Mrads.

This invention can be embodied in containers for holding body fluids, blood systems, blood transfusion systems, catheters, conduits for blood transfer, and dialysis tubes.

Now, the present invention will be described more specifically below with reference to working examples.

EXAMPLES 1-3 AND CONTROL 1

In a Henschel mixer, 100 parts by weight of polyvinyl chloride of an average polymerization degree of about 1,050 and varying amounts of di-2-ethylhexyl phthalate (DOP) and dioctyl maleate (DOM) indicated in Table 1 and a suitable amount of stabilizer generally used in a vinyl chloride resin composition were kneaded by stirring until thorough adsorption of plasticizer. The resultant mixture was pelletized by an extruding machine. To test for dynamic thermal stability, the resultant vinyl chloride resin composition was placed in a 100-ml laboplast mill(product to Toyo Precision Machinery Co.) and kneaded under the conditions of 180 C. of fixed temperature and 120 r.p.m. of blade revolution number for the determination of properties of resin (kneading torque and resin temperature) during the course of fabrication. During the test, the rise time of normal torque (time for decomposition) was clocked. The results are shown in Table 1.

TABLE 1

| Formulation (parts by weight) | Example 1 | Example 2 | Example 3 | Control 1 |
|---|---|---|---|---|
| PVC (P = 1,050) | 100 | 100 | 100 | 100 |
| DOP | 35 | 35 | — | 40 |
| DOM | 5 | 5 | 40 | — |
| Lubricant | 1.0 | 0 | — | 1.0 |
| Dynamic stability steady torque (kg.cm) | 120 | 120 | 120 | 120 |
| Constant temperature (°C.) | 188 | 188 | 188 | 188 |
| Decomposition time (min.) | 44.6 | 43.5 | 67.0 | 23.5 |

It is noted from Table 1 that the vinyl chloride resin compositions according to the present invention are notably better than the conventional control in terms of decompositon time.

EXAMPLES 4-5 AND CONTROL 2

With rolls, 100 parts by weight of polyvinyl chloride having an average polymerization degree of about 1,050, varying amounts of di-2-ethylhexyl phthalate (DOP), dioctyl maleate (DOM), and dibutyl maleate (DBM) indicated in Table 2 and suitable amounts of stabilizer and lubricant normally used in apparatuses for medical treatment were kneaded. Then, the resultant mixture was press molded into a sheet about 2 mm in thickness.

The sheet so produced was exposed to gamma ray of intensity of 3 Mrads. The sheet was tested for coloration along the course of time. The results are shown in Table 2.

The sheet was tested for hygienic safety as specified by the "Vinyl Chloride Resin Blood Set Standard (Ministry of Health and Welfare Standard)" published by Ministreal Notice No. SHO 40(1965)-448. The results are shown in Table 2. Hemolytic toxicity and cellular toxicity were rated by the intracompany standard.

TABLE 2

| Formulation (parts by weight) | Example 4 | Example 5 | Control 2 |
|---|---|---|---|
| PVC (P = 1,050) | 100 | 100 | 100 |
| DOP | 30 | 30 | 30 |
| DOM | 10 | — | — |
| DBM | — | 5 | — |

TABLE 2-continued

| Formulation (parts by weight) | Example 4 | Example 5 | Control 2 |
|---|---|---|---|
| Condition of coloration | | | |
| Before exposure | No color, transparent | No color, transparent | No color, transparent |
| Immediately after exposure (3 Mrads) | No color, transparent | No color, transparent | No color, transparent |
| One day after exposure (60° C.) | No color, transparent | No color, transparent | Brown, transparent |
| Three days after exposure (60° C.) | No color, transparent | No color, transparent | Dark brown, Semi-transparent |
| Safety | | | |
| Δ PH | 0.3 | 0.4 | 0.4 |
| Δ KMnO$_4$ | 0.6 | 0.9 | 0.7 |
| Hemolytic toxicity | No recognized | No recognized | No recognized |
| Cellular toxicity | No recognized | No recognized | No recognized |

It is noted from Table 2 that the vinyl chloride resin compositions according with the present invention avoid being colored even by radiation and are better than the conventional control in terms of safety.

EXAMPLE 6 AND CONTROLS 3–4

Pressed sheets were obtained by following the procedure of Example 4, except that dibutyl fumarate (Example 6), dibutyl itaconate (Control 3), and octyl acrylate (Control 4) were used each in an amount of 5 parts by weight. The sheets were exposed to gamma ray at 3 Mrads and tested for condition of coloration. The results are shown in Table 3.

TABLE 3

| | Example 6 | Control 3 | Control 4 |
|---|---|---|---|
| | $C_4H_9OCOCH=CHCOOC_4H_9$ | $C_4H_9OCO(=CH_2)CH_2COOC_4H_9$ | $CH=CHCOOC_8H_{17}$ |
| | Dibutyl fumarate | Dibutyl itaconate | Octyl acrylate |
| Before exposure | No color, transparent | No color, transparent | No color, transparent |
| Immediately after exposure (3 Mrad) | No color, transparent | No color, transparent | No color, transparent |
| One day after exposure (60° C.) | No color, transparent | Brown, transparent | Brown, transparent |
| Three days after exposure (60° C.) | No color, transparent | Dark brown, semitransparent | Dark brown semitransparent |

It is noted from the results of Table 3 that the medical instrument made of vinyl chloride resin composition incorporating an unsaturated dicarboxylic dialkyl ester of the structure represented by the general formula I of the present invention avoids being colored even by radiation, whereas the apparatus formed of vinyl chloride resin composition incorporating an ester of a chemical structure similar to but not of the general formula I is not effective in preventing coloration by radiation.

As described above, the vinyl chloride resin composition of the present invention comprises 100 parts by weight of vinyl chloride resin, 0.1 to 50 parts by weight of an unsaturated aliphatic dicarboxylic dialkyl ester, and 0 to 200 parts by weight of other plasticizer. This composition, therefore, enjoys high safety, exhibits excellent stability to withstand heat, excels in dynamic thermal stability, and represses deterioration of resin due to residence within a fabricating machine during the course of fabrication, and eliminates the problems of coloration of resin due to interruption of the work of fabrication and occurrence of black extraneous portion in the shaped article due to inclusion of resin which had a long residence time. The composition enjoys high safety and excels in stability to resist heat, light, and radiation and, even on exposure to radiation for the purpose of sterilization, avoids becoming colored with passage of time, and satisfies the standard for acceptance as a medical instrument. When medical instruments are made of the vinyl chloride resin composition, they exhibit outstanding effects.

These effects are manifested more conspicuously when $R_3$ and $R_4$ in the general formula I each denote a hydrogen atom or methyl group and when the mumber of carbon atoms in the alkyl groups of $R_1$ and $R_2$ falls in the range of 3 to 15. Medical instruments which function most advantageously are obtained when the unsaturated aliphatic dicarboxylic dialkyl esters are selected from among maleic dialkyl esters and fumaric dialkyl esters, preferably from among dioctyl maleate, dibutyl maleate, dioctyl fumarate, and dibutyl fumarate.

Further, since the medical instrument according to the present invention does not utilize such heavy metal as lead or cadmium as a stabilizer, it enjoys high safety on the human system and functions more advantageously than the conventional type.

What is claimed is:

1. A vinyl chloride resin composition, comprising component (1) 100 parts by weight of vinyl chloride resin, component (2) 5 to 40 parts by weight of an unsaturated aliphatic dicarboxylic dialkyl ester represented by the formula I:

$$R_1OCOCR_3=CR_4COOR_2 \qquad (I)$$

wherein $R_1$ and $R_2$ independently denote an alkyl group having 4 to 10 carbon atoms and $R_3$ and $R_4$ independently denote a group represented by the formula II: —$C_nH_{2n+1}$ wherein n denotes an integer of the value of 0 to 6, and component (3) 0 to 200 parts by weight of a plasticizer which is not said component (2).

2. The vinyl chloride resin composition according to claim 1, wherein the symbol n in the general formula II denotes 1 or 0.

3. The vinyl chloride resin composition according to claim 1, wherein the symbols $R_3$ and $R_4$ in the general formula I each denote hydrogen atom.

4. The vinyl chloride resin composition according to claim 1, wherein either of the symbols $R_3$ and $R_4$ in the general formula I denotes methyl group and the other symbol denotes hydrogen atom.

5. The vinyl chloride resin composition according to claim 1, wherein the number of carbon atoms in the alkyl groups of $R_1$ and $R_2$ in the general formula I is from 3 to 15.

6. The vinyl chloride resin composition according to claim 1, wherein said unsaturated aliphatic dicarboxylic dialkyl ester is a maleic dialkyl ester or a fumaric dialkyl ester.

7. The vinyl chloride resin composition according to claim 6, wherein said maleic dialkyl ester or fumaric dialkyl ester is in an amount of 0.5 to 40 parts by weight.

8. The vinyl chloride resin composition according to claim 1, wherein said unsaturated aliphatic dicarboxylic dialkyl ester is dibutyl maleate, dibutyl maleate, dioctyl 9. The vinyl chloride resin composition according to claim 8, wherein said dibutyl maleate or dibutyl fumarate is in an amount of 5 to 20 parts by weight.

10. The vinyl chloride resin composition according to claim 1, wherein said plasticizer is a phthalic dialkyl ester, the alkyl groups of which each has 6 to 13 carbon atoms.

11. The vinyl chloride resin composition according to claim 1, wherein said plasticizer is an epoxy hexahydrophthalic dialkyl ester.

12. The vinyl chloride resin composition according to claim 2, wherein $R_3$ and $R_4$ are each a hydrogen atom and $R_1$ and $R_2$ are each an alkyl group having from 3 to 15 carbon atoms.

13. The vinyl chloride resin composition according to claim 1, wherein one of $R_3$ and $R_4$ is the methyl group and the other is a hydrogen atom.

14. The vinyl chloride resin composition according to claim 8, wherein said unsaturated aliphatic dicarboxylic dialkyl ester is a maleic dialkyl ester or a fumaric dialkyl ester.

15. The vinyl chloride resin composition according to claim 14, wherein said unsaturated aliphatic dicarboxylic dialkyl ester is dioctyl maleate, dibutyl maleate, dioctyl fumarate or dibutyl fumarate.

16. The vinyl chloride resin composition according to claim 15, wherein said dioctyl maleate or dioctyl fumarate is incorporated in an amount of 2 to 40 parts by weight.

17. The vinyl chloride resin composition according to claim 15, wherein said dibutyl maleate or dibutyl fumarate is incorporated in an amount of 5 to 20 parts by weight.

18. The vinyl chloride resin composition according to claim 14, wherein said plasticizer is a phthalic dialkyl ester the alkyl groups of which each has 6 to 13 carbon atoms.

19. The vinyl chloride resin composition according to claim 15, wherein said plasticizer is a phthalic dialkyl ester the alkyl groups of which each has 6 to 13 carbon atoms.

* * * * *

UNITED STATES PATENT AND TRADEMARK OFFICE
CERTIFICATE OF CORRECTION

PATENT NO. : 4,740,545
DATED : April 26, 1988
INVENTOR(S) : Y. OHACHI

It is certified that error appears in the above-identified patent and that said Letters Patent is hereby corrected as shown below:

In the title page, under "OTHER PUBLICATIONS",
    "Einflub" should read --Einfluss--.

Column 1, line 44: following "undergo", insert --a--.

Column 3, line 33, "weigh" should read --weight--.

Column 3, line 47, "ingeger" should read --integer--.

Column 8, line 59, "Ministreal" should read --Ministereal--.

Column 10, line 11, "mumber" should read --number--.

Column 11, claim 8, last line, following "dioctyl", insert
    --fumarate, or dibutyl fumarate--.

Signed and Sealed this

Twenty-first Day of April, 1992

Attest:

HARRY F. MANBECK, JR.

*Attesting Officer*  *Commissioner of Patents and Trademarks*